United States Patent [19]
Schaffer et al.

[11] Patent Number: 5,174,954
[45] Date of Patent: Dec. 29, 1992

[54] PALLADIUM ALLOYS FOR DENTAL IMPLANT RESTORATIONS

[75] Inventors: Stephen P. Schaffer, Hamburg; Patrick J. McCabe, Tonawanda, both of N.Y.; Bernt-Roger Gustafsson, Maersta, Sweden

[73] Assignee: Ivoclar N.A., Amherst, N.Y.

[21] Appl. No.: 662,001

[22] Filed: Mar. 1, 1991

[51] Int. Cl.$^5$ .................................. C22C 5/04
[52] U.S. Cl. .................................. 420/463; 420/465; 433/200.1; 433/207
[58] Field of Search ............. 420/463, 465; 148/430, 148/431; 433/200.1, 207

[56] References Cited

U.S. PATENT DOCUMENTS

| | | | |
|---|---|---|---|
| 3,137,571 | 6/1964 | Cooper | 420/463 |
| 4,387,072 | 1/1983 | Schaffer | 420/463 |
| 4,399,096 | 8/1983 | Agarwal | 420/463 |
| 4,526,750 | 7/1985 | Cascone | 420/463 |
| 4,539,176 | 9/1985 | Cascone | 420/463 |
| 4,569,825 | 2/1986 | Dvivedi et al. | 420/464 |
| 4,576,789 | 3/1986 | Prasad | 420/463 |
| 4,591,483 | 5/1986 | Nawaz | 420/463 |
| 4,619,810 | 10/1986 | Prasad | 420/463 |
| 4,943,483 | 7/1990 | Ingersoll et al. | 420/463 |

*Primary Examiner*—John P. Sheehan
*Attorney, Agent, or Firm*—Cushman, Darby & Cushman

[57] ABSTRACT

The present invention relates to alloys containing about 50-90% palladium, 0-37% gold, 0-3% platinum, 0-35% silver, 0.5-8% gallium, 0-8% tin, and up to 0.2% of a grain refiner selected from the group consisting of iridium, rhenium and ruthenium, or mixtures thereof. In order to withstand the forces of mastication over long spans or cantilever sections, the alloys are more rigid than conventional palladium based alloys. The alloys may be utilized for conventional crown and bridgework or may be fabricated into a number of different prostheses for use on dental implants. These applications include, for example, metal base plates for dentures, metal retaining bars for removable or fixed removable dentures, full metal coverage crowns and bridges, and metal substructures to be veneered with resin or porcelain materials.

9 Claims, 1 Drawing Sheet

PALLADIUM ALLOYS FOR DENTAL IMPLANT RESTORATIONS

BACKGROUND OF THE INVENTION

1. Technical Field

The present invention relates to palladium-based alloys and uses thereof. In particular, such alloys may be used in dental restorations, and more specifically, in dental implant restorations.

2. Background Information

It is well known that alloys to be used in the oral environment should provide a high degree of biocompatability and inertness to the conditions in the mouth. When these alloys are placed in electrical contact with metallic or other electrically conductive implants, it also becomes necessary to consider the possibility and potential results of galvanic coupling between dissimilar metals. The existence of a galvanic couple can cause the more anodic or active metal to corrode at an accelerated rate compared to the same material in an uncoupled situation. If an implant is made from titanium or titanium alloy, it is important to use an alloy for the superstructure that is at least as noble, or cathodic, as the titanium. Palladium base alloys achieve this level of nobility.

As with all alloys which may be used with dental porcelains, it is important to have a solidus temperature above 1100° C. This allows sufficient temperature between the firing temperature of porcelain and the onset of melting of the alloy to allow soldering of the alloy. Additionally, to allow the alloy to be melted and cast with standard equipment in the dental laboratory the liquidus temperature should not exceed 1400° C.

In order to obtain compatibility between the alloy and typical dental porcelains it is important for the alloy to exhibit a coefficient of thermal expansion between 13.9 and $15.2 \times 10^{-6}/C$. This will result in the porcelain being placed into compression after firing which will impart the greatest strength to the ceramic veneering material.

Due to the difficulty of placing implants in the posterior region of the jaw, it is quite common in implant restorations for the superstructure to include a cantilever or unsupported extension posterior to the last abutment (see FIG. 1). If this section deforms excessively under the forces of mastication, the occlusal relationship between mandibular and maxillary arches will be altered in these regions. It is important, therefore, that the alloy used in the superstructure possess a rigidity that can withstand these masticatory forces.

Traditional gold-based alloys have been used for dental crown and bridge work for many years (see U.S. Pat. No. 3,574,611). Being electrochemically as noble as titanium, these alloys are suitable for use with titanium implants for an electrochemical standpoint. However, these alloys lack the strength and rigidity necessary to withstand the forces applied to cantilevered extensions. Newer palladium-based alloys have increased strength and rigidity over the gold-based alloys (see, e.g., U.S. Pat. No. 3,819,366 and U.S Pat. No. 4,400,350). However, in long span cantilever sections, even they may not possess sufficient rigidity to resist masticatory forces.

It is therefore an object of the present invention to provide a novel palladium alloy which meets all of the requirements for conventional crown and bridge fabrication as well as an alloy that possesses increased rigidity to provide support in cantilevered designs.

SUMMARY OF THE INVENTION

The present invention relates to alloys that consist essentially, by weight, of about 50-95% palladium, 0-37% gold, 0-3% platinum, 0-35% silver, 0.5-8% gallium, 0-8% indium, 0-8% tin and up to 0.2% of a grain refiner selected from the group consisting of rhenium, ruthenium and iridium or mixtures thereof.

In particular, the alloys described herein can be grouped into three different embodiments based upon the percentages of the elements contained therein.

More specifically, the first embodiment relates to an alloy consisting essentially, by weight, of about 50-61% palladium, 35-40% gold, 0.5-2.5% silver, 2-8% gallium, 0-8% indium, 0-8% tin, 0.01-0 1% rhenium and 0.01-0.1% ruthenium.

The second embodiment includes an alloy consisting essentially, by weight, of about 50-61% palladium, 25-37% silver, 1.8-3% gold, 4-7% tin, 0.5-3% gallium, 0.5-3% indium, 0-2% platinum. 0.01-0.1% rhenium and 0.01-0.1% ruthenium.

The third embodiment of the present invention includes an alloy consisting essentially, by weight, of about 77-95% palladium, 2-3% gold, 2-3% silver, 0-6% gallium, 0-6% indium, 0-6% tin, 0.01-0.1% rhenium and 0.01-0.1% ruthenium.

The alloys may be fabricated into a number of different types of prostheses for use on dental implants. These applications include, for example, metal base plates for dentures, metal retaining bars for removable or fixed removable dentures, and metal substructures to be veneered with resin or porcelain materials.

All U.S. patents and publications refereed to herein are hereby incorporated by reference.

DETAILED DESCRIPTION OF THE INVENTION

Figure 1:
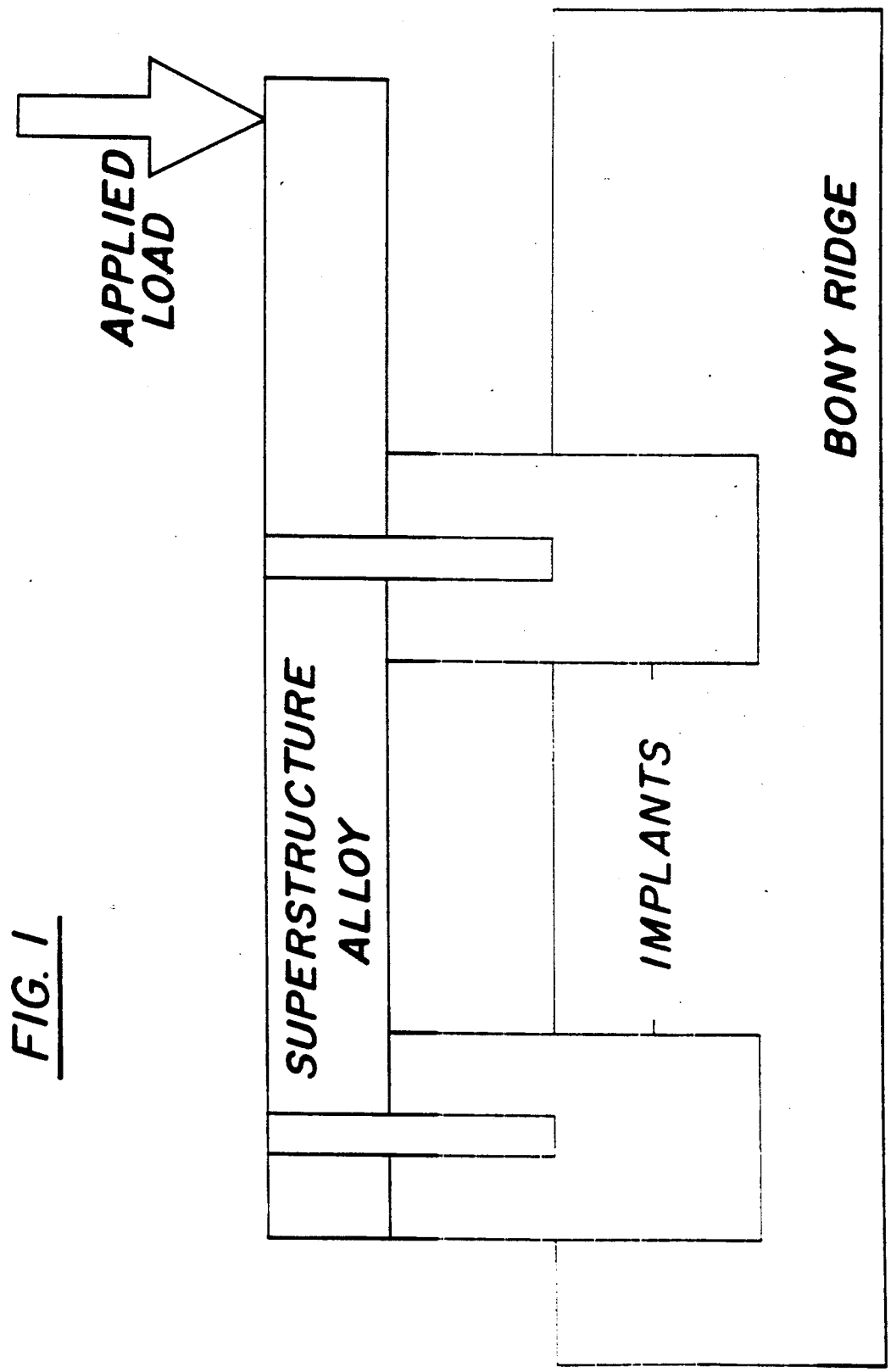
FIG. 1 represents an implant superstructure placed in function on dental implants and showing the load placed on the cantilevered extension.

As indicated above, the alloys of the present invention include palladium as the principal component. Varying amounts of gold, silver, platinum, gallium, indium, and tin are used to achieve the desired properties. Furthermore, minor amounts of other elements may also be included in the alloys.

The preferred embodiments of the present invention fall into three groups. The first embodiment includes an alloy consisting essentially of about 50-61% palladium, 35-40% gold, 0.5-2.5% silver, 0.01-0.1% rhenium, 0.01-0.1% ruthenium, and varying combinations of 2-8% gallium, 0-8% indium, and 0-8% tin. The various amounts of gallium, indium, and tin control the melting range, strength, and modulus of elasticity of the resultant alloy. Basically, all three elements decrease the melting range and increase the strength of the alloy. Their effects on modulus seem to be more synergistic. Thus, various combinations of the three elements produce greater effects that the sum total of the effects of the elements individually.

Additionally, it is preferable to add silver to the alloy to increase the thermal expansion. Without the silver, the alloy of this embodiment tends to have an expansion on the low side of average for porcelain-fused-to-metal alloys. By raising the expansion toward the middle of the range of alloy expansion, one broadens the range of porcelains with which the alloy will be compatible. Also, the silver tends to increase the modulus in conjunction with indium. Furthermore, rhenium and ruthenium provide for effective grain refining. Alloys in this group can develop 0.1% yield strengths over 130,000 psi and elastic moduli in excess of 25,000,000 psi. Yield strength describes the stress at which the alloys or compound begins to function in a plastic manner (Craig, R., *Restorative Dental Materials*, 7th ed., p. 73 (C. V. Mosby Co. 1985)). Elastic modulus refers to the relative stiffness of the material with the range of elasticity (Craig, R., supra at p. 79).

With regard to the first embodiment of the invention, the alloy preferably consists essentially, by weight, of about 55-57% palladium, 36-38% gold, 1-2% silver, 5-7% gallium, 0% indium, 0% tin, 0.04-0.06% rhenium and 0.04-0.06% ruthenium. The alloy, more preferably consists essentially, by weight, of about 55.9% palladium, 37% gold, 1% silver, 6% gallium, 0.05% rhenium and 0.05% ruthenium (see Example One).

The second embodiment includes an alloy consisting essentially, by weight, of about 50-61% palladium 25-37% silver, 0.01-0.1% rhenium and 0.01-0.1% ruthenium with varying combinations of 1.8-3% gold, 4-7% tin, 0.5-3% gallium, 0.5-3% indium, and 0-2% platinum. Rhenium and ruthenium are used for grain refining. Alloys in this group can develop 0.1% yield strengths over 90,000 psi and elastic moduli in excess of 24,000,000 psi.

The alloy of the second embodiment preferably consists essentially, by weight, of about 58-60% palladium, 25-28% silver, 2-3% gold, 5-7% tin, 1-2% gallium, 1-2% indium, 1-2% platinum, 0.04-0.06% rhenium and 0.04-0.06% ruthenium. The alloy more preferably consists essentially, by weight, of about 59.9% palladium, 26% silver, 2.75% gold, 7% tin, 2% gallium, 1.5% indium, 1.0% platinum, 0.05% rhenium and 0.05% ruthenium (see Example One).

The third embodiment includes an alloy consisting essentially of about 77-95% palladium, 2-3% gold, 2-3% silver, 0.01-0.1% rhenium and 0.01-0.1% ruthenium with 0-6% each of gallium, indium, and tin. As in the previous two groups, rhenium and ruthenium are used for grain refining. Alloys in this group can develop 0.1% yield strengths over 100,000 psi and elastic moduli in excess of 24,000,000 psi.

The alloy of the third embodiment of the present invention preferably consists essentially, by weight, of about 80-82% palladium, 2.3-2-7% gold, 2.3-2.7% silver, 4-6% gallium, 2-5% indium, 0-4% tin, 0.05-0.1% rhenium and 0.05-0.1% ruthenium. The alloy more preferably consists essentially, by weight, of about 81.9% palladium, 2.5% gold, 2.5% silver, 6.0% gallium, 3.5% indium, 0.1% rhenium and 0.1% ruthenium (see Example Three).

Gold alloys which could be used for the same purpose have yield strengths of 45-60,000 psi and moduli of 12-14 million psi. However, as can be observed based on these properties, the gold-based alloys are not strong or rigid enough to be used in high stress situations such as in long span bridges and cantilevered sections. Presently known palladium alloys can also generate yield strengths in excess of 100,000 psi, but their moduli are in the range of 14-16 million psi. The increases in the moduli of the alloys of the present invention reduce the amount of distortion that occurs under load, and the high yield strengths provide protection against permanent deformation.

With respect to modifications of the three embodiments set forth above, one could add copper and/or cobalt in place of some or all of the gallium, indium, and/or tin to make the alloys stronger. However, this addition or substitution would tend to make the oxide produced for bonding to porcelain darker in color, and possibly, less desirable. Normally, the alloys discussed above are white in color.

Furthermore, it should be noted that all of the alloys of the present invention can be used in traditional dentistry as well as in implant dentistry. In particular, the alloys are suitable for manufacturing crowns and bridges with or without coverings of resin or porcelain materials. In addition, the alloys of the present invention could also be utilized for jewelry, as a less expensive alternative to white golds.

The production of the alloys does not require any special steps other than those used in the traditional production of dental alloys. Basically, the alloys are melted, usually by induction heating, at atmospheric pressure and usually under the flame of a reducing gas such as, for example, carbon monoxide or natural gas. Vacuum melting is not utilized. (If necessary, the alloys (if hardened) may be remelted either by induction or with a gas-oxygen torch with no additional protection.) The alloys are then cast into a ceramic mold of the desired shape under normal atmospheric condition.

The present invention can be illustrated by the use of the following non-limiting examples.

EXAMPLE ONE

| Composition: | |
|---|---|
| Pd | 56.0% |
| Au | 37.0% |
| Ag | 1.0% |
| Ga | 6.0% |
| In | —% |
| Sn | —% |
| plus grain refiners | |

| Physical & Mechanical Properties: | Porcelain | Hardened |
|---|---|---|
| Yield Strength (0.1% offset) | 80,900 psi | |
| Proof Stress (0.2% offset) | 580 MP | |
| Vickers Hardness | 275 | |
| Elongation | 35% | |
| Modulus of Elasticity (psi) | 18,400,000 | |
| Density (g/cm$^3$) | 13.0 | |
| Melting Range | 2110-2335 F. | 1155-1280 C. |
| Casting Temperature | 2435 F. | 1335 C. |
| Coefficient of Thermal Exp | 14.3 × 10$^{-6}$/°C. | |
| Heat Treatment | | |
| Not Heat Hardenable | | |

Porcelain Compatibility

This alloy was subjected to thermal shock testing with Ceramco II, Crystar, Duceram, Vita, and Will Ceram porcelains. RESULTS PENDING

| Additional Data: | |
|---|---|
| Annealing Temperature | 1500 F. |
| Weighted Sag (1850 F., 5 min) | 0.50 mm |
| Button Test | no porosity |
| Grain Size | 50 microns |

EXAMPLE TWO

| Composition: | |
|---|---|
| Pd | 60.0% |
| Au | 3.0% |
| Ag | 26.0% |
| Pt | 1.0% |
| Ga | 2.0% |
| In | 1.5% |
| Sn | 7.0% |
| plus grain refiners | |

| Physical & Mechanical Properties: | Porcelain | Hardened |
|---|---|---|
| Yield Strength (0.1% offset) | 80,200 psi | 87,300 psi |
| Proof Stress (0.2% offset) | 560 MP | 615 MPa |
| Vickers Hardness | 230 | 265 |
| Elongation | 31% | 28.5% |
| Modulus of Elasticity (psi) | | 18,000,000 |
| Density (g/cm$^3$) | | 11.2 |
| Melting Range | 2110-2335 F. | 1150-1280 C. |
| Casting Temperature | 2435 F. | 1335 C. |
| Coefficient of Thermal Exp | 14.9 $\times$ 10$^{-6}$/°C. | |

Heat Treatment

To Harden: Heat at 1100° F. (595) for 15 minutes, air cool

Porcelain Compatibility

This alloy was subjected to thermal shock testing with Ceramco II, Crystar, Duceram, Vita, and Will Ceram porcelains. RESULTS PENDING

| Additional Data: | |
|---|---|
| Annealing Temperature | 1750 F. |
| Weighted Sag (1850 F., 5 min) | 1.94 mm |
| Button Test | no porosity |
| Grain Size | 13 microns |

EXAMPLE THREE

| Composition: | |
|---|---|
| Pd | 82.0% |
| Au | 2.5% |
| Ag | 2.5% |
| Ga | 6.0% |
| In | 3.5% |
| Sn | 3.5% |
| plus grain refiners | |

| Physical & Mechanical Properties: | Porcelain | Hardened |
|---|---|---|
| Yield Strength (0.1% offset) | 64,500 psi | 67,500 psi |
| Proof Stress (0.2% offset) | 470 MP | 485 MPa |
| Vickers Hardness | 240 | 260 |
| Elongation | 41% | 37% |
| Modulus of Elasticity (psi) | | 21,500,000 |
| Density (g/cm$^3$) | | 11.4 |
| Melting Range | 2130-2435 F. | 1165-1335 C. |
| Casting Temperature | 2535 F. | 1390 C. |
| Coefficient of Thermal Exp | 14.1 $\times$ 10$^{-6}$/°C. | |

Heat Treatment

To Harden: Heat at 1200° F. (650° C.) for 30 minutes, air cool

Porcelain Compatibility

This alloy was subjected to thermal shock testing with Ceramco II, Crystar, Duceram, Vita, and Will Ceram porcelains. The alloy performed well with all porcelains. Note: No failures occurred until 170° C.; after the maximum temperature of 200° C. there were still bridges of Crystar, Duceram, and Will Ceram without any cracks. After completion of the test none of the porcelains exhibited cracks at 100% of the units. This is extremely unusual, and indicates an exceptionally high potential for porcelain compatibility.

| Additional Data: | |
|---|---|
| Annealing Temperature | 1700-1600 |
| Weighted Sag (1850 F., 5 min) | 0.74 mm |
| Button Test | no porosity |
| Grain Size | 30 microns |

EXAMPLE FOUR

| Constituents of Alloys | Weight % | Properties of Alloy |
|---|---|---|
| Pd | 54.9 | 0.1% Offset Yield Strength - 133,000 psi |
| Au | 37.0 | Modulus of Elasticity - 18,000,000 psi |
| Ga | 8.0 | |
| Re | 0.05 | |
| Ru | 0.05 | |

EXAMPLE FIVE

| Constituents of Alloys | Weight % | Properties of Alloy |
|---|---|---|
| Pd | 51.9 | 0.1% Offset Yield Strength - 133,000 psi |
| Au | 37.0 | Modulus of Elasticity - 18,000,000 psi |
| Ag | 2.5 | |
| In | 6.0 | |
| Ga | 2.5 | |
| Re | 0.05 | |
| Ru | 0.05 | |

EXAMPLE SIX

| Constituents of Alloys | Weight % | Properties of Alloy |
|---|---|---|
| Pd | 59.9 | 0.1% Offset Yield Strength - 94,400 psi |
| Au | 27.0 | Modulus of Elasticity - 20,400,000 psi |
| Ag | 3.0 | |
| Sn | 7.0 | |
| Ga | 3.0 | |
| Re | 0.05 | |
| Ru | 0.05 | |

EXAMPLE SEVEN

| Constituents of Alloys | Weight % | Properties of Alloy |
|---|---|---|
| Pd | 57.9 | 0.1% Offset Yield Strength - 94,400 psi |
| Ag | 29.0 | Modulus of Elasticity - 20,400,000 psi |
| Au | 3.0 | |
| Sn | 7.0 | |
| Ga | 0.5 | |
| In | 2.5 | |
| Re | 0.05 | |
| Ru | 0.05 | |

EXAMPLE EIGHT

| Constituents of Alloys | Weight % | Properties of Alloy |
|---|---|---|
| Pd | 76.8 | 0.1% Offset Yield Strength - 109,000 psi |
| Au | 2.5 | Modulus of Elasticity - 16,500,000 psi |
| Ag | 2.5 | |
| Ga | 6.0 | |
| In | 6.0 | |
| Sn | 6.0 | |
| Re | 0.1 | |
| Ru | 0.1 | |

EXAMPLE NINE

| Constituents of Alloys | Weight % | Properties of Alloy |
|---|---|---|
| Pd | 82.8 | 0.1% Offset Yield Strength - 66,600 psi |
| Au | 2.5 | Modulus of Elasticity - 25,300,000 psi |
| Ag | 2.5 | |
| Ga | 6.0 | |
| In | 6.0 | |
| Re | 0.1 | |
| Ru | 0.1 | |

What is claimed is:

1. A palladium-based alloy for use in dental implant restorations consisting essentially, by weight, of essentially about 50-61% palladium, 35-40% gold, 0.5-2.5% silver, 2-8% gallium, 0-8% indium, 0-8% tin, 0.01-0.1% rhenium, and 0.01-0.1% ruthenium.

2. The alloy of claim 1 consisting essentially, by weight, of about 55-57% palladium, 36-38% gold, 1-2% silver, 5-7% gallium, 0.04-0.06% rhenium, and 0.04-0.06% ruthenium.

3. The alloy of claim 2 consisting essentially, by weight, of about 55.9% palladium, 37% gold, 1% silver, 6% gallium, 0.05% ruthenium and 0.05% rhenium.

4. A palladium-based alloy for use in dental implant restorations consisting essentially, by weight, of essentially about 50-61% palladium, 25-37% silver, 1.8-3% gold, 4-7% tin, 0.5-3% gallium, 0.5-3% indium, 0-2% platinum, 0.01-0.1% rhenium and 0.01-0.1% ruthenium.

5. The alloy of claim 4 consisting, by weight, of about 58-60% palladium, 25-28% silver, 2-3% gold, 5-7% tin, 1-2% gallium, 1-2% indium, 1-2% platinum, 0.04-0.06% rhenium, and 0.04-0.06% ruthenium.

6. The alloy of claim 5 consisting essentially, by weight, of about 59.9% palladium, silver, 2.75% gold, 7% tin, 2% gallium, 1.5% indium, 1% platinum, 0.05% rhenium and 0.05% ruthenium.

7. A palladium-based alloy for use in dental implant restorations consisting, by weight, of about 77-95% palladium, 2-3% gold, 2-3% silver, 0-6% gallium, 0-6% indium, 0-6% tin, 0.01-0.1% rhenium, and 0.01-0.1% ruthenium.

8. The alloy of claim 7 consisting, by weight, of about 80-82% palladium, 2.3-2.7% gold, 2,3-2.7% silver, 4-6% gallium, 2-5% indium, 0-4% tin, 0.05-0.10% rhenium, and 0.05-0.10% ruthenium.

9. The alloy of claim 8 consisting, by weight, of about 81.9% palladium, 2.5% gold, 2.5% silver, 6% gallium, 3.5% indium, 3.4% tin, 0.1% rhenium and 0.1% ruthenium.

* * * * *